United States Patent
Myllykangas

(10) Patent No.: US 11,786,178 B2
(45) Date of Patent: Oct. 17, 2023

(54) ELECTRODE STRUCTURE OF BIO-SIGNAL MEASUREMENT AND ELECTRODE SYSTEM

(71) Applicant: BITTIUM BIOSIGNALS OY, Kuopio (FI)

(72) Inventor: Juha Myllykangas, Kuopio (FI)

(73) Assignee: BITTIUM BIOSIGNALS OY, Kuopio (FI)

( * ) Notice: Subject to any disclaimer, the term of this patent is extended or adjusted under 35 U.S.C. 154(b) by 881 days.

(21) Appl. No.: 16/590,521

(22) Filed: Oct. 2, 2019

(65) Prior Publication Data
US 2021/0100510 A1 Apr. 8, 2021

(51) Int. Cl.
*A61B 5/00* (2006.01)
*H01R 4/04* (2006.01)
*H01R 13/24* (2006.01)
*A61B 5/259* (2021.01)

(52) U.S. Cl.
CPC ............ *A61B 5/6833* (2013.01); *A61B 5/259* (2021.01); *A61B 5/7225* (2013.01); *H01R 4/04* (2013.01); *H01R 13/2407* (2013.01); *A61B 2562/164* (2013.01); *A61B 2562/225* (2013.01); *H01R 2201/12* (2013.01)

(58) Field of Classification Search
CPC ........ A61B 5/28; A61B 5/6823; A61B 5/6833
See application file for complete search history.

(56) References Cited

U.S. PATENT DOCUMENTS

| | | | |
|---|---|---|---|
| 6,415,169 B1 * | 7/2002 | Kornrumpf | A61B 5/282 600/382 |
| 2011/0077497 A1 | 3/2011 | Oster et al. | |
| 2015/0073231 A1 | 3/2015 | Beck et al. | |
| 2015/0087951 A1 | 3/2015 | Felix et al. | |

FOREIGN PATENT DOCUMENTS

JP 2005137456 A * 6/2005 ......... A61B 5/04085

OTHER PUBLICATIONS

Extended European Search Report issued in EP App No. 20 19 9144 dated Feb. 11, 2021, 8 pages.

* cited by examiner

*Primary Examiner* — Eun Hwa Kim
(74) *Attorney, Agent, or Firm* — Nixon & Vanderhye PC

(57) ABSTRACT

An electrode structure of a bio-signal measurement comprises electrodes adapted to be adhered on skin with an adhesive and separated from each other. A connector arrangement for an electric contact with an external electric device is on an opposite side of the electrode structure. Electric conductors are electrically connected with the electrodes and the connector arrangement. The electrode structure comprises attachable sections directly adjacent to one of the at least two electrodes, the attachable sections being adapted to be adhered on the skin. The electrode structure comprises a flexible and elastic loose section, which is free from an adherence to the skin, each of the attachable sections being located between an electrode and a loose section.

20 Claims, 3 Drawing Sheets

ELECTRODE STRUCTURE OF BIO-SIGNAL MEASUREMENT AND ELECTRODE SYSTEM

FIELD

The invention relates to an electrode structure of a bio-signal measurement and an electrode system.

BACKGROUND

An electronic device, which measures bio-signals such as ECG (ElectroCardioGram) and EEG (ElectroEncephaloGram), must have the electrodes of a patch electrode well contacted with the skin, and therefore the patch electrode is attached to the skin with an adhesive gel during the measurement.

When a user of the patch electrode sweats or gets otherwise wet, a continuous moisture layer from electrode to electrode on the skin forms an electrical conductor between the electrodes, which causes a short cut of varying impedance. The short cut substantially weakens the measurement signal from the electrodes. In the long run, a cumulative effect of the sweat becomes more and more significant. Additionally, the patch electrode of only one size is not an optimum size for all users. A larger patch electrode, where a distance between the electrodes is longer, would be better for a taller user and a smaller patch electrode, where the distance between the electrodes is shorter, would be better for a shorter user. Furthermore, when a user moves, the patch electrode experiences twisting, compressive and/or stretching forces, which may deteriorate the attachment of the electrodes to the skin despite the adhesive, which, in turn, may disturb the measurement.

Hence, improvement is needed.

BRIEF DESCRIPTION

The present invention seeks to provide an improvement in the bio-signal measurements.

The invention is defined by the independent claims. Embodiments are defined in the dependent claims.

LIST OF DRAWINGS

Example embodiments of the present invention are described below, by way of example only, with reference to the accompanying drawings, in which FIG. 1 illustrates an example of an electrode structure;

DESCRIPTION OF EMBODIMENTS

The following embodiments are only examples. Although the specification may refer to "an" embodiment in several locations, this does not necessarily mean that each such reference is to the same embodiment(s), or that the feature only applies to a single embodiment. Single features of different embodiments may also be combined to provide other embodiments. Furthermore, words "comprising" and "including" should be understood as not limiting the described embodiments to consist of only those features that have been mentioned and such embodiments may contain also features/structures that have not been specifically mentioned. All combinations of the embodiments are considered possible if their combination does not lead to structural or logical contradiction.

It should be noted that while Figures illustrate various embodiments, they are simplified diagrams that only show some structures and/or functional entities. The connections shown in the Figures may refer to logical or physical connections. It is apparent to a person skilled in the art that the described apparatus may also comprise other functions and structures than those described in Figures and text. It should be appreciated that details of some functions, structures, and the signalling used for measurement and/or controlling are irrelevant to the actual invention. Therefore, they need not be discussed in more detail here.

Figure 1:
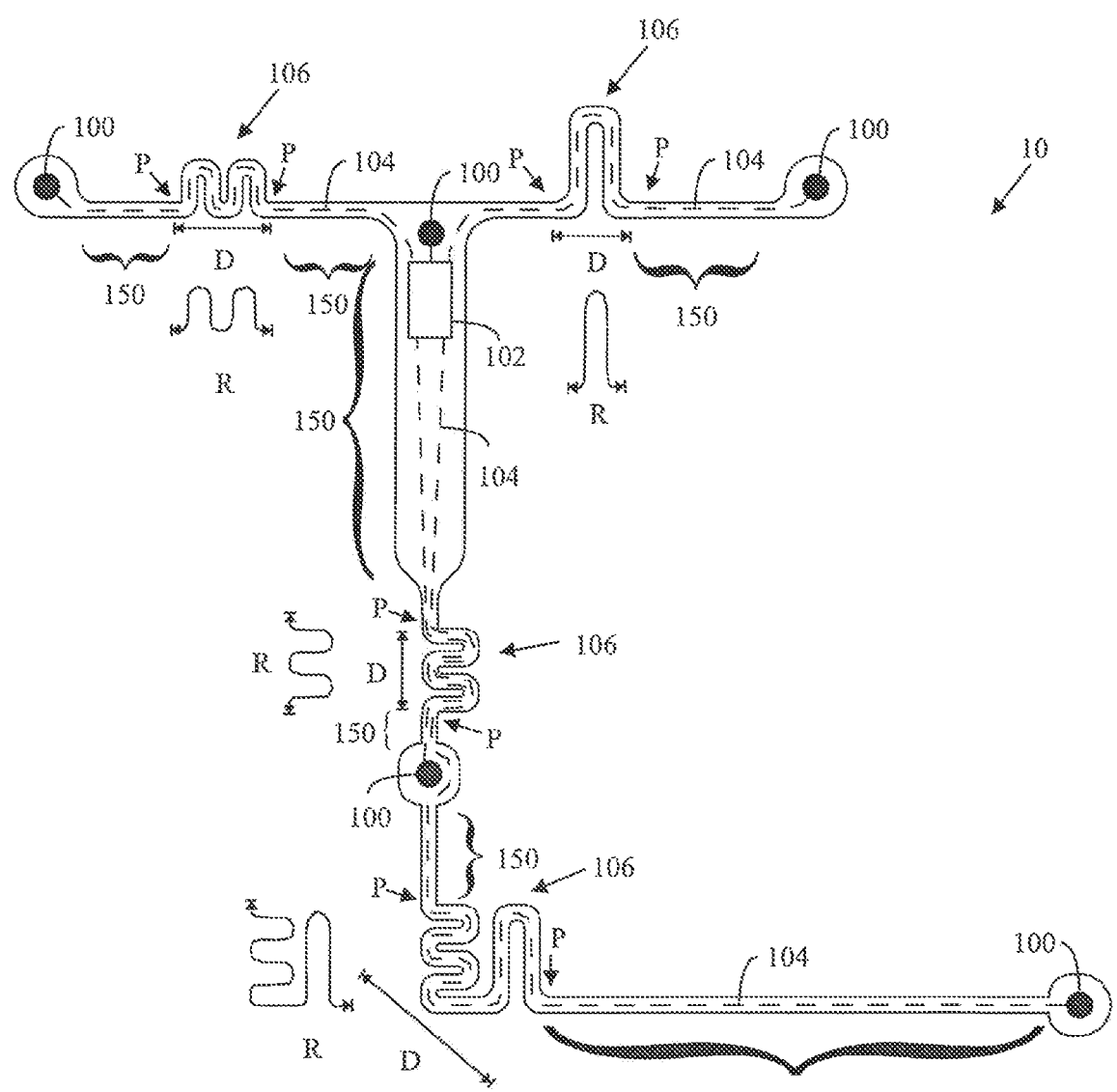

FIG. 1 illustrates an example of an electrode structure 10 which provides a bio-signal for a measurement. The electrode structure 10 comprises at least two electrodes 100, which are adapted to be adhered on the skin 300 (see FIG. 3) of a mammal with an adhesive 302 (see FIG. 3), are separated from each other in a longitudinal direction of the electrode structure 10. The mammal may be a human or an animal. The electrode structure 10 may be flat like a sheet. The electrode structure 10 may resemble a patch and it may be called a patch electrode. The longitudinal direction refers to a direction that extends parallel to a surface of the electrode structure 10 and is different from a direction of thickness of the electrode structure 10. The thickness of the electrode structure 10 is small with respect to a square root of an area of the electrode structure 10 or even an area of the single side that faces the skin 300 during the measurement.

The electrode structure 10 also comprises a connector arrangement 102 for an electric contact with an external electric device 200, the connector arrangement 102 being on an opposite side of the electrode structure 10 in a transverse direction of the electrode structure 10. The transverse direction is parallel to the thickness of the electrode structure 10.

In an embodiment an example of which is shown in FIG. 1, the electrode structure 10 may further comprise electrical conductors 104, which extend in both the longitudinal and transverse directions within the electrode structure 10. The electrical conductors 104 are electrically connected with the at least two electrodes 100 and the connector arrangement 102.

The electrode structure 10 comprises at least one attachable section 150 directly adjacent to or in physical contact with one of the at least two electrodes 100, each of the attachable sections 150 being adapted to be adhered on the skin 300. The attachable sections 150 may be adhered to the skin 300 with glue in corresponding manner to the electrodes 100.

The electrode structure 10 also comprises at least one loose section 106 between as shown in FIG. 1. Each of the attachable sections 150 is located between one of the at least one electrode 100 and one of the at least one loose section 106. Each of the loose sections 106 is flexible, elastic, and free from an adherence to the skin 300 when the electrode structure 100 is applied on the skin 300. That is, no adhesive is used between the skin 300 and the loose section 106. The attachable sections 150 may be stiff and/or straight. That is, the attachable sections 150 may be non-flexible and/or non-stretchable. The attachable sections 150 may be the curveless or less curved than the loose sections 106.

The attachable sections 150 increase the adherence and thus protect the electrodes 100 from forces which are caused by clothes and the movement of the skin 300 and which might otherwise loosen the electrodes 100 or cause artefacts to the measurement signal.

The attachable sections 150 also limit the length of the loose sections 106 such that the loose sections 150 do not hit or stick with clothes, for example.

In an embodiment, a percentage of a length of a loose section 106 and a combined length of attachable sections 150 and the loose section 106, which are between any two electrodes 100, which the attachable sections 150 are directly adjacent to, may be 5% to 30%. In an embodiment, a percentage of a length of a loose section 106 and a combined length of attachable sections 150 and the loose section 106, which are between any two electrodes 100, which the attachable sections 150 are directly adjacent to, may be 15% to 25%. In an embodiment, a percentage of a length of a loose section 106 and a combined length of attachable sections 150 and the loose section 106, which are between any two electrodes 100, which the attachable sections 150 are directly adjacent to, may be about 15%. In an embodiment, a percentage of a length of a loose section 106 and a combined length of attachable sections 150 and the loose section 106, which are between any two electrodes 100, which the attachable sections 150 are directly adjacent to, may be about 25%.

In an embodiment an example of which is illustrated in FIG. 1, the electrode structure 10 comprises the at least one loose section 106 between the connector arrangement 102 and each of the at least two electrodes 100.

Figure 2:
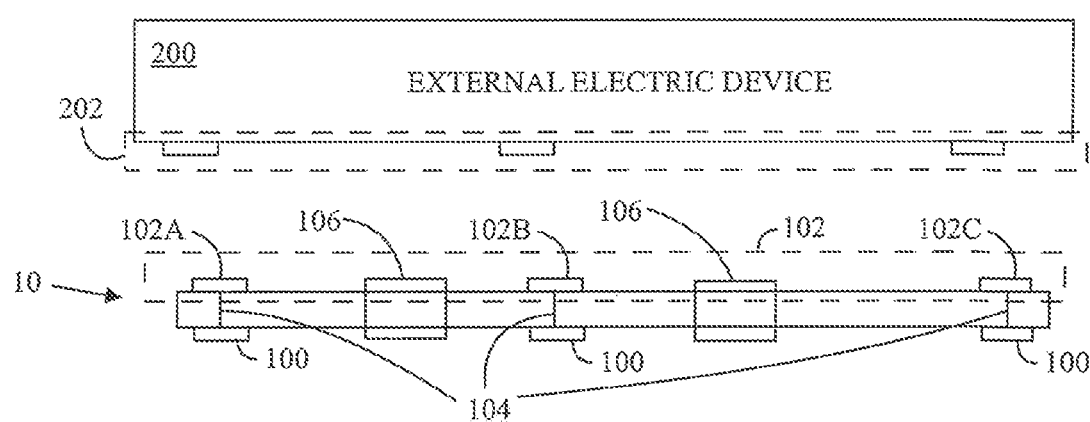
FIG. 2 illustrates an example of an electrode structure and an external device.

FIG. 2 illustrates an example where the connector arrangement 102 comprises separate connectors 102A, 102B, 102C for contacting the external electric device 200. The external electric device 200 comprises counter connectors 202, which are suitable for electric and mechanic connection with the connectors 102A to 102C, the electric and mechanic connection being also releasable and potentially repeatable. The connectors 102A to 102C may comprise tool-less connectors, for example. In an embodiment, which is illustrated in FIG. 1, the connector arrangement may comprise an USB-connector (Universal Serial Bus), for example.

Figure 3:
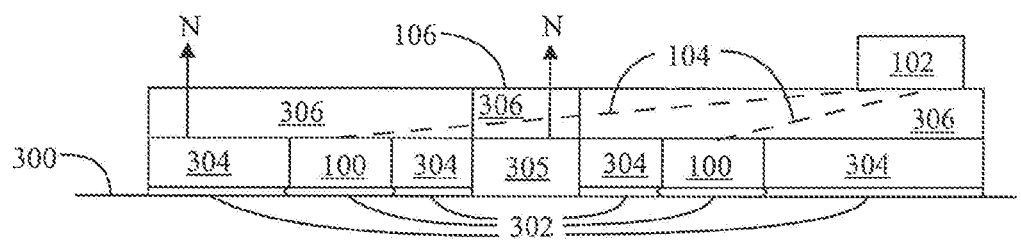
FIG. 3 illustrates an example of layers of an electrode structure.

In an embodiment an example of which is illustrated in FIG. 3, the electrode structure 10 may comprise a substrate layer 304, 305. The at least two electrodes 100 are attached to the substrate 304, 305 and are separated from each other in a direction perpendicular to a normal N of the substrate layer 304, 305. The connector arrangement 102 may be attached over the substrate 304, 305 on the opposite side of the electrode structure 10 in a direction parallel to the normal N of the substrate layer 304, 305. The electrical conductors 104 may extend in both the perpendicular and parallel directions to the normal N within the electrode structure 10.

The substrate layer 304 may be made of threads of woven or non-woven fabric of plant or animal fibers. Additionally or alternatively, the substrate layer 304 may be made of felted fabric of plant or animal fibers. The substrate layer 304 may be made of textile. The substrate layer 304 may be made of breathable, soft and/or skin-friendly material, as it is usual for a gear of a physical activity. The substrate layer 304 may be made of non-woven spun lace, for example. The substrate layer 304 may be attached to the skin 300 with an adhesive 302. That is the substrate layer 304 may have glue on both sides in order to have a reliable attachment to both the skin 300 and the conductor layer 306 where the conductors 104 are located. The substrate layer 305 at each of the at least one loose section 106 has no adhesive against the skin 300, but there may be glue between the substrate layer 305 and the conductor layer 306. That is, the substrate layer 305 has adhesive only on one side.

In an embodiment, the substrate layer 305 may be made of material that does not absorb water. In an embodiment, the substrate layer 305 may be made of material that is water repellant. In an embodiment, the substrate layer 305 may be made of material that is elastic. In an embodiment, the substrate layer 305 may be made of material that has at least one of the properties mentioned above. In an embodiment, the substrate layer 305 may be made of polyester liner, for example.

The substrate layer 304 comprises the at least one attachable section 150 each directly adjacent to or in physical contact with one of the at least two electrodes 100. The substrate layer 305 comprises the at least one loose section 106 such that each of the attachable sections 150 is located between one of the at least one electrode 100 and one of the loose sections 106.

FIG. 1 illustrates an embodiment where a route R along a loose section 106 between points P on opposite ends of each of the at least one loose section 106 may be longer than a direct distance D between said points P.

In an embodiment an example of which is shown in FIG. 1, at least one of the at least one loose section 106 may be meandering such that the electrode structure 10 has, at the loose section 106, a winding and turning shape.

In an embodiment an example of which is shown in FIG. 1, at least one of the at least one loose section 106 may have the electrode structure 10 zig-zagged. The route R along a loose section 106 between the points P on the opposite ends of any of the at least one loose section 106 is longer than a direct distance D between said points P.

In an embodiment, at least one of the at least one loose section 106 may comprise at least one breakable bridge 400, which materialistically connects length increasing sections 402 of the electrode structure 10 on opposite sides of at least one turn 404 of loose section 106. In an embodiment, the breakable bridge 400 may be made of a material which breaks when the loose section 106 is stretched using a predetermined force. When the breakable bridge 400 breaks, it is cut into two or more pieces.

In an embodiment, the breakable bridge 400 may have weakened section 401, which is configured to break when the loose section 106 is stretched using a predetermined force. The force of the bridge 400 limiting the stretching of the electrode structure 10 may be such that a person putting on the electrode structure 10 (himself/herself or for other human or animal), feels the limitation in his fingers. The breakable bridge 400 may be elastic such that it adapts to a stretch up to a predetermined amount before breaking. In that manner, the person does not stretch the electrode structure 10 up to its extreme when applying the electrode structure 10 on the skin 300. However, when a person or an animal, which has the electrode structure 10 attached on his/her/its skin 300, moves, the movement may result in stretching, twisting and compressing forces to the electrode structure 10, which may cause the at least one bridge 400 break letting the loose section 106 freely give in to the forces affecting it.

In an embodiment where the conductor layer 306 comprises a pattern of the electrical conductors 104, the electric conductors 104 are covered with electrically insulating material layer for electrical insulation from the skin 300.

By having at least one loose section 106 in the electrode structure 10, sweat and/or moisture cannot easily form a continuous moisture layer between the electrodes 100. Additionally, the electrode structure 10 is easy to stretch or compress to an optimum size for users of different sizes. Furthermore, when a user moves, the electrode structure 10 experiences twisting, compressive and/or stretching forces, which cause minimized or no deterioration of attachment of the electrodes to the skin because the loose section 106 automatically adapts to the forces.

Figure 5:
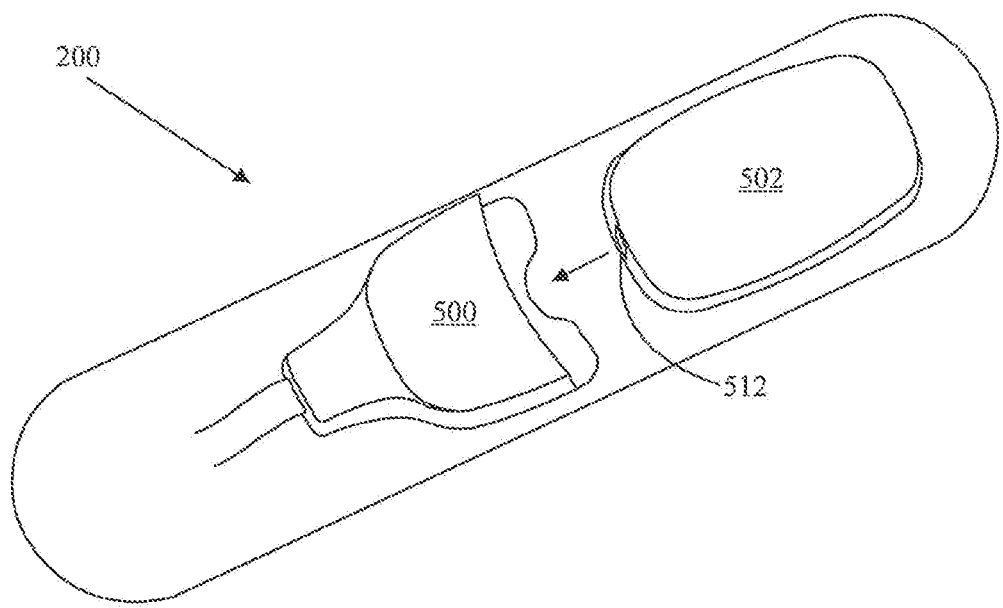
FIG. 5 illustrate an example of an external device.

FIG. 5 illustrates an example of the external electric device 200, which may have a polymer holder 500 for a bio-signal processing device 502. The name refers to the fact that the polymer holder 500 is made of polymer such as plastic. The bio-signal processing device 502 may be an electronic device which may convert an analog bio-signal it receives to a digital bio-signal. The bio-signal processing device 502 may also filter the bio-signal in the analog or in the digital form. Additionally or alternatively, the bio-signal processing device 502 may perform data processing of the bio-signal, and it may also store data of the bio-signal and/or a result of its processing. The bio-signal may be related to body movement, body temperature, heart rate variability, electrocardiogram, electromyogram, electroencephalogram or the like for example.

The arrow in FIG. 5 illustrates the feature that the bio-signal processing device 502 can be inserted in the polymer holder 500.

Figure 6:
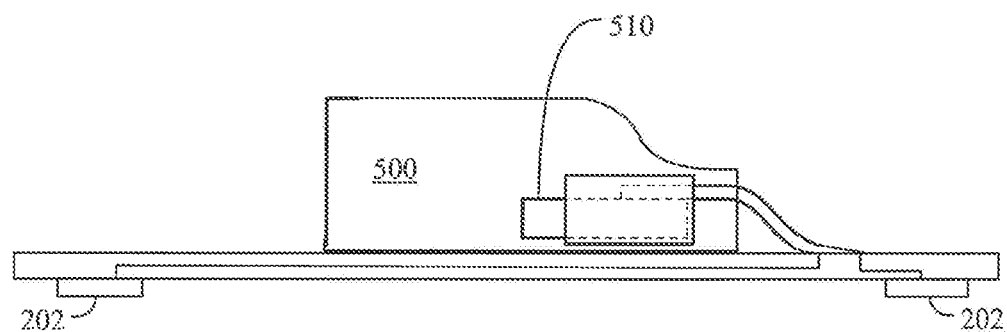
FIG. 6 illustrates an example of a connector of an external device.

In an embodiment an example of which is illustrated in FIG. 6, the external electric device 200 may include the polymer holder 500, which may comprise a male connector 510. The male connector 510 may connect with a female connector 512 of the bio-signal processing device 502 in response to the insert of the bio-signal processing device 502 in the pocket 506.

In an embodiment, the male connector may be a male USB connector (USB=Universal Serial Bus), and the female connector of the bio-signal processing device 502 may be a female USB connector. Alternatively, the male connector 510 may be in the bio-signal processing device 502 and the female connector 512 may be in the polymer holder 500. The counter-connectors 202 can be coupled with the connector arrangement 102 of the electrode structure 10.

Figure 4:
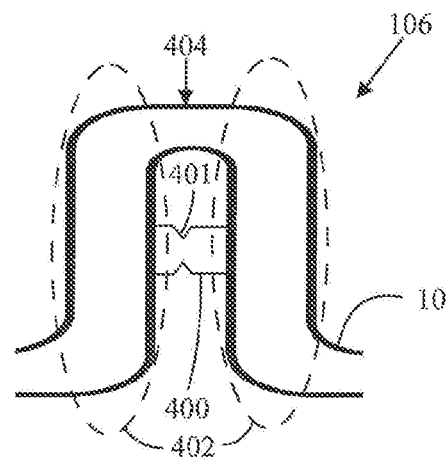
FIG. 4 illustrates an example of a loose section of an electrode structure.
Figure 7:
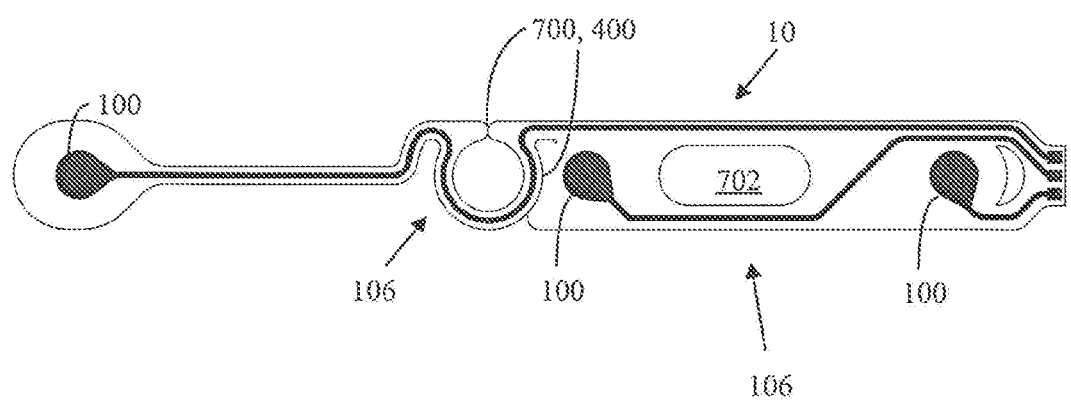
FIG. 7 illustrates of an example of electrode structure with round cuts for loose sections.

FIG. 7 illustrates an example of the electrode structure 10. One of the loose sections 106 has one or more cuts 700, where the electrode structure 10 is fully or partly cut in a vertical direction. If the electrode structure 10 is fully cut at the cuts 700, the cuts 700 will widen into a gap when the loose section 106 is under a stretching force. If the electrode structure 10 is partly cut at the cuts 700, the cuts 700 are like breakable bridges 400 (see FIG. 4). Still, the cuts 700 will widen into a gap when the loose section 106 is under a stretching force which breaks the at least one bridge. In an embodiment, at least one of the cuts 700 (full or partial) has a round shape, which minimizes the number of sharp edges. The sharp edges may namely break easily. In general, round shapes of the cuts 700 are more durable in use.

Another of the loose sections 106 has thinner material thickness because of a hole 702 in the structure. The thinner material stretches more easily.

It will be obvious to a person skilled in the art that, as technology advances, the inventive concept can be implemented in various ways. The invention and its embodiments are not limited to the example embodiments described above but may vary within the scope of the claims.

The invention claimed is:

1. An electrode structure of a bio-signal measurement system, wherein the electrode structure comprises:
at least two electrodes separated from each other in a longitudinal direction of the electrode structure;
a connector arrangement configured to form an electric contact with an external electric device on a side of the electrode structure opposite to that of the at least two electrodes;
electrical conductors, which are electrically connected with the at least two electrodes and the connector arrangement;
at least one attachable section directly adjacent to one of the at least two electrodes, each said attachable section being adapted to be adhered on the skin of a mammal with an adhesive; and
at least one loose section configured to be flexible, elastic, and free from an adherence to the skin when the electrode structure is applied on the skin, each said attachable section being located between one of the at least two electrodes and one of the at least one loose sections;
wherein at least one said loose section is formed by first and second sections connected to one another by at least one turn and comprises a breakable bridge, the first and second sections adapted to extend generally parallel to one another and in a direction transverse to the longitudinal direction of the electrode structure when the electrode structure is applied on the skin, the breakable bridge being spaced apart from the at least one turn and from the skin when the electrode structure is applied on the skin;
wherein the breakable bridge is an elastic strip comprising a weakened section, which is configured to mechanically break, when the loose section is stretched using a predetermined force;
wherein the breakable bridge has an elasticity sufficient to enable a person to feel in his/her fingers a limit of stretchability of the electrode structure when applying the electrode structure on the skin.

2. The electrode structure of claim 1, wherein the electrode structure comprises the at least one loose section between the connector arrangement and each of the at least two electrodes.

3. The electrode structure of claim 1, wherein the electrical conductors are configured to extend in both the longitudinal and transverse directions within the electrode structure.

4. The electrode structure of claim 1, wherein the at least two electrodes are attached to a substrate and are separated from each other in a direction perpendicular to a normal of the substrate layer;
the connector arrangement is attached over the substrate on the opposite side of the electrode structure in a direction parallel to the normal of the substrate layer; and
the electrical conductors are configured to extend in both the perpendicular and parallel directions to the normal within the electrode structure.

5. The electrode structure of claim 1, wherein a route along the at least one loose section between points on opposite ends thereof is longer than a direct distance between said points.

6. The electrode structure of claim 1, wherein at least one of the at least one loose sections has a winding and turning shape.

7. The electrode structure of claim 1, wherein at least one of the at least one loose sections has the electrode structure zig-zagged, and a zig-zagged route between points on the opposite ends thereof is longer than a direct distance between said points.

8. The electrode structure of claim 1, wherein the electrical conductors are covered with electrically insulating material for electrical insulation at the at least one loose section.

9. The electrode structure of claim 1, wherein the breakable bridge is stretchable up to a predetermined amount before breaking.

10. The electrode structure of claim 9, wherein the weakened section is a cut in the breakable bridge.

11. An electrode system comprising:
an external electric device configured to filter a bio-signal in analog or digital form, perform data processing of the bio-signal, and store data of the bio-signal and/or a result of its processing, and
an electrode structure configured to provide the bio-signal, the electrode structure comprising:
at least two electrodes separated from each other in a longitudinal direction of the electrode structure;
a connector arrangement configured to form an electric contact with the external electric device on a side of the electrode structure opposite to that of the at least two electrodes;
electrical conductors, which are electrically connected with the at least two electrodes and the connector arrangement;
at least one attachable section directly adjacent to one of the at least two electrodes, each said attachable section being adapted to be adhered on the skin of a mammal with an adhesive; and
at least one loose section configured to be flexible, elastic, and free from an adherence to the skin when the electrode structure is applied on the skin, each said attachable section being located between one of the at least two electrodes and one of the at least one loose sections;
wherein at least one said loose section is formed by first and second sections connected to one another by at least one turn and comprises a breakable bridge, the first and second sections adapted to extend generally parallel to one another and in a direction transverse to the longitudinal direction of the electrode structure when the electrode structure is applied on the skin, the breakable bridge being spaced apart from the at least one turn and from the skin when the electrode structure is applied on the skin;
wherein the breakable bridge is an elastic strip comprising a weakened section, which is configured to mechanically break, when the loose section is stretched using a predetermined force;
wherein the breakable bridge has an elasticity sufficient to enable a person to feel in his/her fingers a limit of stretchability of the electrode structure when applying the electrode structure on the skin.

12. The electrode system of claim 11, wherein the electrode structure comprises the at least one loose section between the connector arrangement and each of the at least two electrodes.

13. The electrode system of claim 11, wherein the electrical conductors are configured to extend in both the longitudinal and transverse directions within the electrode structure.

14. The electrode system of claim 11, wherein the at least two electrodes are attached to a substrate and are separated from each other in a direction perpendicular to a normal of the substrate layer;
the connector arrangement is attached over the substrate on the opposite side of the electrode structure in a direction parallel to the normal of the substrate layer; and
the electrical conductors are configured to extend in both the perpendicular and parallel directions to the normal within the electrode structure.

15. The electrode system of claim 11, wherein a route along of the at least one loose section between points on opposite ends thereof is longer than a direct distance between said points.

16. The electrode system of claim 11, wherein at least one of the at least one loose sections has a winding and turning shape.

17. The electrode system of claim 11, wherein at least one of the at least one loose sections has the electrode structure zig-zagged, and a zig-zagged route between points on the opposite ends thereof is longer than a direct distance between said points.

18. The electrode system of claim 11, wherein the electrical conductors are covered with electrically insulating material for electrical insulation at the at least one loose section.

19. The electrode structure of claim 11, wherein the breakable bridge is stretchable up to a predetermined amount before breaking.

20. The electrode system of claim 19, wherein the weakened section is a cut in the breakable bridge.

* * * * *